US010030168B2

(12) United States Patent
Srivastava et al.

(10) Patent No.: US 10,030,168 B2
(45) Date of Patent: Jul. 24, 2018

(54) HIGH REFRACTIVE INDEX MATERIAL

(71) Applicant: MOMENTIVE PERFORMANCE MATERIALS INC., Waterford, NY (US)

(72) Inventors: Rajiv Srivastava, Glenmont, NY (US); Douglas Michael Dukes, Troy, NY (US); Hai Hui Lin, Naperville, IL (US)

(73) Assignee: MOMENTIVE PERFORMANCE MATERIALS INC., Waterford, NY (US)

(*) Notice: Subject to any disclaimer, the term of this patent is extended or adjusted under 35 U.S.C. 154(b) by 0 days.

(21) Appl. No.: 14/400,844

(22) PCT Filed: Mar. 7, 2013

(86) PCT No.: PCT/US2013/029614
§ 371 (c)(1),
(2) Date: Nov. 13, 2014

(87) PCT Pub. No.: WO2013/172921
PCT Pub. Date: Nov. 21, 2013

(65) Prior Publication Data
US 2015/0184022 A1 Jul. 2, 2015

Related U.S. Application Data

(60) Provisional application No. 61/646,511, filed on May 14, 2012.

(51) Int. Cl.
| C09D 183/04 | (2006.01) |
| C08G 77/392 | (2006.01) |
| C07F 7/08 | (2006.01) |
| C08G 77/38 | (2006.01) |
| C08K 5/00 | (2006.01) |
| C08K 5/548 | (2006.01) |
| C08G 77/20 | (2006.01) |

(52) U.S. Cl.
CPC .......... C09D 183/04 (2013.01); C07F 7/0814 (2013.01); C08G 77/38 (2013.01); C08G 77/392 (2013.01); C08K 5/0091 (2013.01); C08K 5/548 (2013.01); C08G 77/20 (2013.01)

(58) Field of Classification Search
CPC .... C09D 183/08; C08G 77/392; C07F 7/0814
See application file for complete search history.

(56) References Cited

U.S. PATENT DOCUMENTS

| 2,640,833 A * | 6/1953 | DiGiorgio ................. C07F 7/12 528/30 |
| 4,049,675 A | 9/1977 | Kanner |
| 4,100,172 A | 7/1978 | Mui |
| 4,808,687 A * | 2/1989 | Burns .................... C08G 77/54 528/30 |
| 5,661,210 A | 8/1997 | Burns et al. |
| 7,863,392 B2 | 1/2011 | Nakanishi et al. |
| 2001/0022565 A1* | 9/2001 | Kimura ................ G09G 3/3266 345/82 |
| 2002/0161140 A1 | 10/2002 | Yoneda et al. |
| 2003/0162929 A1 | 8/2003 | Verbruggen et al. |
| 2004/0116640 A1 | 6/2004 | Miyoshi |
| 2004/0178509 A1 | 9/2004 | Yoshino et al. |
| 2005/0212008 A1 | 9/2005 | Miyoshi |
| 2006/0073347 A1 | 4/2006 | Morita et al. |
| 2007/0073026 A1 | 3/2007 | Miyoshi |
| 2007/0112147 A1 | 5/2007 | Morita et al. |
| 2007/0197742 A1 | 8/2007 | Yamakawa |
| 2007/0218299 A1 | 9/2007 | Azechi |
| 2008/0033120 A1 | 2/2008 | Yoshitake et al. |
| 2008/0262158 A1 | 10/2008 | Morita et al. |
| 2009/0118440 A1 | 5/2009 | Nakanishi et al. |
| 2009/0146175 A1 | 6/2009 | Bahadur et al. |
| 2009/0179180 A1 | 7/2009 | Morita et al. |
| 2010/0060829 A1 | 3/2010 | Tsuchida |
| 2010/0276721 A1 | 11/2010 | Yoshitake et al. |
| 2010/0301377 A1 | 12/2010 | Kato et al. |
| 2011/0143149 A1 | 6/2011 | Shibayama |

FOREIGN PATENT DOCUMENTS

| JP | S525758 | 1/1977 |
| JP | 8134358 A | 5/1996 |
| JP | 2000169714 A | 6/2000 |
| JP | 2006-257321 | 9/2006 |
| JP | 2006299099 A | 11/2006 |
| JP | 2006324596 A | 11/2006 |
| JP | 2009185226 A | 8/2009 |
| JP | 2010-59114 | 3/2010 |

(Continued)

OTHER PUBLICATIONS

Freeman (Silicones, Published for The Plastics Institute, Iliffe Books Ltd, 1962, pp. 86-87).*
International Search Report and Written Opinion of the International Searching Authority, PCT/US2013/029614 dated May 3, 2013.
Asai et al., "Synthesis of silyl-functionalized oligothiophene-based polymers with bright blue light-emission and high refractive index", Journal of Organometallic Chemistry 696 (2011) 1236-1243.
Haramotoa, Yuichiro et al., "New side chain liquid crystalline polysiloxanes containing 1,3-dithiane or 1,3-dioxane rings as mesogenic side groups", Liquid Crystals (1997) vol. 23, No. 2, 263-267.
Bouillon, Jean-Phillippe et al., "Synthesis of a New Type of Bis(acylsilanes) Starting from 2-Alkyl- or 2-Phenyl-1,3-dithiane and Bis (chlorinted) Disilane or Disiloxane", Synthesis (2002), No. 4, 552-556.

(Continued)

Primary Examiner — Kuo Liang Peng
(74) Attorney, Agent, or Firm — Joseph Waters; McDonald Hopkins LLC

(57) ABSTRACT

A high refractive index molecule and high refractive index polymers comprising such monomers. The high refractive index monomer comprises a carrier atom having a high refractive index group attached thereto, the high refractive index group comprising a heterocyclic compound comprising at least one sulfur atom.

35 Claims, No Drawings

(56) References Cited

FOREIGN PATENT DOCUMENTS

| WO | 2009120434 | A1 | 10/2009 |
|----|------------|----|----|
| WO | 2009154261 | A1 | 12/2009 |
| WO | WO2010021290 | | 2/2010 |

OTHER PUBLICATIONS

Supplementary European Search Report of the European Searching Authority dated Oct. 1, 2015 for EP 13790068.

\* cited by examiner

HIGH REFRACTIVE INDEX MATERIAL

CROSS REFERENCE TO RELATED APPLICATIONS

This application is a 35 U.S.C. 371 national stage filing and claims priority to PCT Application No. PCT/US2013/029614, entitled "High Refractive Index Material" filed on Mar. 7, 2013, which claims the benefit of U.S. Provisional Application No. 61/646,511 entitled "High Refractive Index Material" filed on May 14, 2012, both of which are incorporated herein in their entirety by reference.

FIELD

The present technology relates to high refractive index materials. More particularly, the present invention relates to a silicone material with a high refractive index. High refractive index materials may be suitable for use in a variety of applications including optical applications such as, for example, as a coating on contact lenses, intraocular lenses, solid state lighting (light emitting diodes, organic light emitting diodes, laser diodes), waveguides (both planar and "fiber" geometries), optical computing, optical storage media, antireflection coatings, conformal coatings, optical lenses, microlenses, automobile topcoats, paint formulations, hair care products, gradient refractive index optical components, and dynamic gradient refractive index components.

BACKGROUND

Siloxane polymers or copolymers having a high refractive index have been increasingly used for a variety of optical applications including, for example, in contact lenses, intraocular lenses, etc. Such polymers are also finding their way into other optical applications requiring high transmission and high refractive index including but not limited to, solid state lighting (light emitting diodes, organic light emitting diodes, laser diodes), waveguides (both planar and "fiber" geometries), optical computing, optical storage media, antireflection coatings, conformal coatings, optical lenses, microlenses, automobile topcoats, paint formulations, hair care products, gradient refractive index optical components, dynamic gradient refractive index components, etc.

Depending on the application, the polymers and products formed from such polymers may need to exhibit a wide range of properties including sufficient structural integrity, strength, elasticity and elongation, index of refraction, etc. In some applications, the polymers must exhibit these properties when formed into a thin film. For example, in intraocular lenses, the lens must be thin and pliable for insertion through a small incision in intraocular lens applications, be able to regain its original shape after incision, and have sufficient structural integrity and strength to retain such shape under normal use conditions.

Introduction of aromatic groups is now a general approach to increase the refractive index of siloxane polymers, and conventional co-polymers for high refractive index applications consist of dimethylsiloxane-phenylmethylsiloxane co-polymers or dimethylsiloxane-diphenylsiloxane co-polymers as described in, for example, U.S. Pat. Nos. 3,996,189; 5,147,396; 5,444,106; and 5,236,970, JP10305092, EP 0335312, WO 93/21245, and WO 95/17460. At a phenyl content of approximately 15 mole %, a polydimethyl siloxane/methylphenyl siloxane co-polymer has a refractive index of 1.462, (*Eur. Polymer J.* 1998, 34, 1727-1733).

Despite the positive effect on the refractive index, the introduction of refractive index modifying groups, such as phenyl-groups, in polysiloxanes is known to result in several disadvantages. Materials formed from siloxanes containing phenyl groups can have reduced flexibility, poor mechanical strength and elasticity, and they can also be hard and brittle. Further, materials with phenyl content greater than 40 mol % are not easily processed and tend to exhibit poor mechanical strength. This limits the refractive index that can be achieved to about 1.54.

One remedy to the problem of vulnerability to cracking is to reinforce the optical structure and improve its mechanical properties by combining the polymer with a solid filler material. Mostly, finely powdered silica is used as a filler material for this purpose. This filler material has a refractive index of 1.46. Since differences in the refractive index of the filler material and the polymer are not allowable in an optical lens, the maximum refractive index of a lens containing such filler material is ultimately 1.46.

In addition to issues with mechanical properties, the incorporation of phenyl into the silicones also makes resulting polymers more vulnerable under thermal and UV-exposure conditions. This results in yellowing of the optical material and transmission losses such that the transmission level is below a tolerable level and can lead to mechanical failure of a device in the optical components. There is a need for alternative means of altering the refractive index of siloxanes.

SUMMARY

The present invention provides high refractive index polymer compositions of matter, methods of making the same, and their utility in several applications. In one aspect, the invention provides high refractive index polymers that allow for a reduction, or even the elimination, of phenyl groups in such polymers, but have a refractive index comparable to or better than phenyl containing siloxanes. In one embodiment, the high refractive index material has a refractive index of about 1.4 or greater, 1.42 or greater, 1.5 or greater, 1.55 or greater, even 1.6 or greater, or even 1.65 or greater.

In one aspect, a high refractive index material comprises a polymer backbone comprising a plurality of high refractive index groups attached thereto, where at least one of the high refractive index groups comprises a heterocyclic structure comprising at least one sulfur atom.

In another aspect, the present invention provides a high refractive index material comprising a polysiloxane having a plurality of high refractive index groups attached thereto, at least one of the high refractive index groups comprising heterocyclic structure comprising at least one sulfur atom. In one embodiment, the heterocyclic structure is a five or six membered ring, comprising at least two sulfur atoms. In one embodiment, the heterocyclic structure is a saturated heterocyclic structure.

In one embodiment, the high refractive index group is directly bonded to a silicon atom in the polymer backbone.

In one embodiment, the high refractive index group is provided as part of a high refractive index monomer, where the high refractive index monomer comprises pendant group attached to a silicon atom on the polymer backbone.

In one aspect, the present invention provides a molecule comprising a carrier atom and a high refractive index functional group, the molecule having the formula:

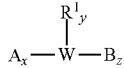

(1)

where W is the carrier atom, $R^1$ is independently chosen from hydrogen, hydroxyl, or a group containing C1-C30 carbon atoms chosen from a linear or branched alkyl radical, a linear or branched alkoxy radical, an alkylvinyl radical (including allyl), a cycloalkyl radical, a branched or linear alkenyl radical, a cycloalkenyl radical, a linear or branched alkynyl radical, an aryl radical, a substituted aryl radical, or a polynuclear aromatic group; A is chosen from a high refractive index group comprising a sulfur-containing heterocyclic structure; B is chosen from a halide, alkoxy (OR), hydroxyl, a alkylvinyl radical (including allyl), hydrogen, —$(CH_2)_n$SH, —$(CH_2)_n$NH$_2$, a glycidyl radical, or a combination of two or more thereof; n is 1-10, x is at least 1; y ranges from zero to two less than the valence of the carrier atom: z is at least 1; 1≤x+y≤one less than the valence of the carrier atom; and x+y+z is equal to the valence of the carrier atom.

In one embodiment, the carrier atom is chosen from silicon, phosphorous, nitrogen, germanium, or carbon.

In one embodiment, the molecule comprises a saturated heterocyclic compound comprising at least one sulfur atom, an unsaturated heterocyclic compound comprising at least one sulfur atom, or a combination of two or more thereof. In one embodiment, the heterocyclic compound comprises two sulfur atoms. In one embodiment, the heterocyclic compound comprises three sulfur atoms. In one embodiment, the heterocyclic compound further comprises one or more non-sulfur heteroatoms.

In one embodiment, the heterocyclic compound is a 3-10 member ring. In one embodiment, the heterocyclic compound is a 5-6 member ring.

In one embodiment, the molecule is of the formula:

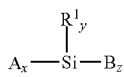

(1A)

where silicon (Si) is the carrier atom, $R^1$ is independently chose from hydrogen, hydroxyl, a linear or branched alkyl radical, a linear or branched alkoxy radical, an aryl radical, an alkylvinyl radical or a combination of two or more thereof; A is independently chosen from a high refractive index group comprising a sulfur-containing heterocyclic structure; B is independently chosen from a halide, OH, OR, a vinyl radical, hydrogen, an allyl radical, —$(CH_2)_n$SH, —$(CH_2)_n$NH$_2$, a glycidyl radical, or a combination of two or more thereof; n is 1-10, x is at least 1; y is 0-2: z is at least 1; 1≤x+y≤3; and x+y+z is 4.

In one embodiment, the molecule is of the formula:

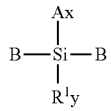

(2)

In one embodiment, the molecule is of the formula:

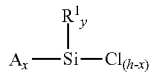

(3A)

where h+y is 4, and h is at least 2.

In one embodiment, the heterocyclic compound is chosen from thiophene (tetrahydrothiophene), 1,3 dithiolane, tetrahydro-2H-thiopyran, 1,3 dithiane, 1,4 dithiane, 1,3,5 dithiane, 1,3,5 dithiazinane, or a combination of two or more thereof.

In another aspect, the present invention provides a polysiloxane polymer or copolymer having a siloxane backbone and comprising a molecule in accordance with aspects of the invention.

In one embodiment, the carrier atom of the molecule is incorporated into the backbone of the polymer and the high refractive index functional group is pendent to the carrier atom.

In one embodiment, the molecule is pendant to the siloxane backbone of the polymer.

In one embodiment, the polymer has a refractive index of at least 1.42; at least 1.50; at least 1.55; at least 1.60. In one embodiment, the polymer has a refractive index of about 1.42 to about 1.65.

In one embodiment, the polymer is described by the formula $M^1_k M^2_j D^1_a D^2_b D^3_d D^4_e T^1_c T^2_i Q_f$ where $M^1$ and $M^2$ are independently $R^2R^3R^4SiO_{1/2}$; $D^1$, $D^2$, $D^3$, and $D^4$ are independently $R^5R^6SiO_{2/2}$; $T^1$ and $T^2$ are independently $R^7SiO_{3/2}$; Q is $SiO_{4/2}$; $R^2$-$R^7$ groups are independently chosen from hydrogen, hydroxyl, a linear or branched alkyl radical, a linear or branched alkoxy radical, an aryl radical, an alkylvinyl radical, amide, amino-groups, propyl-mercapto groups, glycidyl-containing groups, a high refractive index sulfur-containing heterocyclic compound, or a high refractive index molecule pendant group, where at least one of $R^2$-$R^7$ is chosen from (1) a high refractive index molecule of Formula 1, or (2) a sulfur-containing heterocyclic compound; a is from 1-1000, b is from 0-500, c is from 0-500, d is from 0-100, e is from 0-100, f is from 0-100, g is from 1-1000, h is from 0-1000, and i is from 0 to 200.

In one embodiment, the polymer is described by the formula $MD_aD^{OL}_dD^H_eT_cQ_fM$, $M^HD_aD^{Ph}_bD^{OL}_dD^H_eT_c$-$Q_fM^H$, $M^HD_aD^{Ph}_bD^{OL}_dT_cQ_fM^H$, $MD_aD^{OL}_dD^{vi}_gT_cQ_fM$, $M^{vi}$-$D_aD^{OL}_dD^{vi}_gT_cQ_fM^{vi}$, or $M^{vi}D_aD^{OL}_dT_cQ_fM^{vi}$, where M represents a trialkylsiloxy radical or a dialkylvinylsiloxy, vi represents a vinyl radical, OL represents an high refractive index monomer comprising a sulfur-containing saturated heterocyclic compound, $D^{OL}$ represents an alkylsiloxy comprising a high refractive index monomer, $D^H$ represents an alkyl hydrogen siloxy, $D^{vi}$ represents alkylvinylsiloxy, D represents dialkylsiloxy, $M^{vi}$ represents a dialkylvinyl siloxy, $M^H$ represents a dialkylhydrogen radical, and a, b, c, d, e, f, and g are positive integers.

In one embodiment, the heterocyclic structure comprising at least one sulfur atom is present in an amount of from 0.1 to 40 mol % of the polymer.

In another aspect, the present invention provides compositions comprising such polymers and devices formed therefrom.

DETAILED DESCRIPTION

The present invention provides a molecule comprising a carrier atom and a high refractive index group attached thereto, monomers comprising such molecules, and polymers comprising such monomers. The high refractive index group comprises a heterocyclic compound comprising at least one sulfur atom. In one embodiment, the high refractive index polymer material comprises a polymer and a high refractive index group attached to the polymer. In one embodiment, the present invention provides a high refractive index polysiloxane comprising a polysiloxane polymer backbone having a high refractive index group attached thereto, where the high refractive index group comprises a heterocyclic compound comprising at least one sulfur atom. The high refractive index group comprising a heterocyclic compound comprising at least one sulfur atom may also be referred to herein as a "sulfur-containing heterocyclic compound" or "sulfur-containing high refractive index groups." In one embodiment, the sulfur-containing high refractive index groups may be provided as part of a high refractive index molecule that is attached to the siloxane backbone. In another embodiment, the high refractive index group may be directly attached to an atom in the siloxane backbone.

The high refractive index polymer material may have a refractive index of about 1.4 or greater. In one embodiment, the high refractive index polymer has a refractive index of about 1.42 or greater. In one embodiment, the high refractive index polymer material has a refractive index of about 1.5 or greater, about 1.55 or greater, about 1.6 or greater, about 1.62 or greater, or even about 1.65 or greater. In one embodiment, the high refractive index polymer material has a refractive index of about 1.4 to about 1.7. In another embodiment, the high refractive index polymer material has a refractive index of from about 1.42 to about 1.68. In another embodiment, the high refractive index polymer material has a refractive index of from about 1.45 to about 1.65. In another embodiment, the high refractive index polymer material has a refractive index of from about 1.5 to about 1.63. In another embodiment, the high refractive index material has a refractive index of from about 1.55 to about 1.60. Here as elsewhere in the specification and claims, numerical values may be combined to form new compositions of undisclosed ranges.

Sulfur-Containing High Refractive Index Group

The sulfur-containing high refractive index group comprises a heterocyclic compound comprising at least one sulfur atom. In one embodiment, the heterocyclic compound is a 3-10 membered ring system comprising at least one sulfur atom in the ring. The heterocyclic compound comprising at least one sulfur atom can be a saturated or unsaturated compound. The structures can also be a fused ring systems where both the rings can be aliphatic, one ring aliphatic and one ring aromatic, or even both rings can be aromatic. Non-limiting examples of suitable high refractive index groups include five-membered rings and six membered rings comprising 1, 2, or 3 sulfur atoms in the ring. In one embodiment, the high refractive index group comprises 2 sulfur atoms in the ring. The sulfur atom can be in any suitable form including, for example, oxidized states such as sulfoxides, sulfones, etc. The sulfur-containing heterocyclic compounds may further comprise other heteroatoms in the ring structure including, but not limited to N, P, O, etc. Additionally, the carbon atoms in the heterocyclic compound may be substituted or non-substituted. The carbon atoms may be substituted with any suitable group including, but not limited to, alkyl, aryl, alkoxy, allyl, vinyl, acetyl, amides etc.

Non-limiting examples of suitable sulfur-containing heterocyclic compounds include, thiophene, 1,3-dithiolane, tetrahydro-2H-thiopyran, 1,3-dithiane, 1,4-dithiane, 1,3,5-trithiane, etc., and combinations of two or more thereof.

High Refractive Index Molecule

The high refractive index group may be provided as part of a high refractive index molecule. The high refractive index molecules can be incorporated into a polymer as either a true repeat unit of the polymer, or be incorporated as a pendant group to the polymer chain, to provide a high refractive index polymer. A high refractive index molecule may comprise a carrier atom and one or more sulfur-containing high refractive index groups attached to the carrier atom. The high refractive index molecule can comprise other groups attached to the carrier atom.

In one embodiment, the high refractive index molecule further comprises a reactive group that can be incorporated into the polymer via a number of processes known to those skilled in the art. Non limiting example includes condensation and hydrosilylation chemistries for incorporation of high refractive index molecule to a siloxane polymer or siloxane precursor material, or for incorporating the high refractive index molecule into the backbone of the siloxane polymer.

The high refractive index molecules of the invention comprise a carrier atom and a high refractive index functional group attached to the carrier atom. The carrier atom may be selected as desired for a particular purpose or intended use. Suitable carrier atoms include, but are not limited to tetra-valent (Group IV) elements such as carbon, silicon, germanium, tin, and lead. Additionally, the carrier atom can be of tri-valent or penta-valent elements (Group V), such as phosphorous and nitrogen. In one embodiment, the carrier atom is chosen from carbon, silicon, germanium, phosphorous, and nitrogen. Exemplary carrier atoms are carbon or silicon.

The high refractive index molecules can be a high refractive index monomer that can be employed to form a polymer material. In one embodiment, the high refractive index molecule is a compound of the Formula 1:

where "W" is the carrier atom as described above, "R¹" is independently chosen from hydrogen, hydroxyl, or a group containing C1-C30 carbon atoms chosen from a linear or branched alkyl radical, a linear or branched alkoxy radical, an alkylvinyl radical (including allyl), a cycloalkyl radical, a branched or linear alkenyl radical, a cycloalkenyl radical, a linear or branched alkynyl radical, an aryl radical, a substituted aryl radical, or a polynuclear aromatic group; "A" is chosen from a high refractive index group as described earlier. In most cases the high refractive index groups comprise a sulfur-containing heterocyclic structure; "B" is chosen from a halide (e.g., Cl, Br, F, I), alkoxy (OR), hydroxyl, a alkylvinyl radical (including allyl), hydrogen, —(CH$_2$)$_n$SH, —(CH$_2$)$_n$NH$_2$, a glycidyl radical, or a combination of two or more thereof; n is 1-10, x is at least 1; y ranges from zero to two less than the valence of the carrier atom: z is at least 1; 1≤x+y≤one less than the valence of the carrier atom; and x+y+z is equal to the valence of the carrier atom.

In one embodiment, the high refractive index molecule is a compound of the Formula 1A:

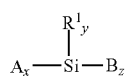

(1A)

where silicon (Si) is the carrier atom, and R$^1$, B, A, x, y, and z are all as described above in Formula 1.

In one embodiment, the high refractive index molecule is a compound of the Formula 1B:

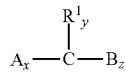

(1B)

where the carrier atom is a carbon atom, and R$^1$, B, A, x, y, and z are all as described above in Formula 1.

In one embodiment, the high refractive index monomer is a compound of the Formula 2:

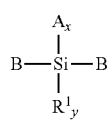

(2)

where A, B, and R$^1$ are as described above in Formula 1. In another embodiment of Formula 2, B is OR and x+y=2 and R can be H, C1-C30 carbon atoms chosen from a linear or branched alkyl radical, a linear or branched alkoxy radical.

It is useful to describe generic molecular building blocks, and their formulas, to provide the basis for writing complex molecular structures. In each instance, the silicon atom is coordinated by four (4) bonds. The four general building block components of siloxanes can be defined as M, D, T, and Q units, listed in order of increasing number of Si—O bonds per unit. M-units have one Si—O bond and thus can be described by the formula: R$^2$R$^3$R$^4$SiO$_{1/2}$, where R$^2$, R$^3$, R$^4$ are independently selected organic groups (with number of carbon). D-units have two Si—O bonds, and thus can be described by the formula: R$^5$R$^6$SiO$_{2/2}$, again, where R$^5$ and R$^6$ are independently selected moieties. T-units have three Si—O bonds, and thus can be described by the formula: R$^7$SiO$_{3/2}$, where R$^7$ is a selected moiety. Finally, Q-units have four Si—O bonds, and can be described by the formula: SiO$_{4/2}$. In this instance, silicon (Si) is coordinated only to the oxygen atoms. Using these four building blocks, descriptive polymer chemistries can be readily assigned using simple constructs. A polymer can incorporate many building block units in a single molecule and as the functional groups R$^2$-R$^7$ change, as in the case of siloxane co-polymers, multiple building blocks of the same type are indicated by different superscripts in the notation. In the description above, the R$^2$-R$^7$ groups are independently chosen from hydrogen, hydroxyl, a linear or branched alkyl radical, a linear or branched alkoxy radical, an aryl radical, an alkylvinyl radical, amide, amino-groups, propyl-mercapto groups, glycidyl-containing groups, a high refractive index sulfur-containing heterocyclic compound, or a high refractive index molecule pendant group. More specifically the alky group can be C1-C13 monovalent substituted and unsubstituted hydrocarbon free radical. Some non-limiting examples include methyl, ethyl, propyl, isopropyl, hexyl, cyclohexyl, cyclopropyl, cyclopentyl etc. The non-limiting examples of aryl radicals may include phenyl, toluyl, napthy. The aryl radical may also include nitrogen and sulfur containing heteroaryls.

In one embodiment, the high refractive index molecule can be generally described by formula 3:

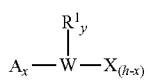

(3)

where W, A, and R$^1$ can be as described above, and X is any halide as described above, h is the original number of X groups before either partially (h>x) or completely (h=x) substituting them with A groups, h+y is 4, x is ≥1 and h≥2. These molecules can be used to form polymer building blocks, equivalent to the siloxane M, D, and T units.

In another embodiment, the high refractive index molecule is a chlorosilane comprising a sulfur-containing high refractive index group. The chlorosilane can be of Formula 3A:

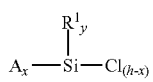

(3A)

where "Si" is the carrier atom and A, R$^1$, and Cl are as described above in Formula 3. The x, y, and h are positive integers and has values as described above. These molecules can be used to form M, D, and T units that can be reacted to form siloxane polymers through the condensation of HCl with the addition of water.

In another embodiment, the high refractive index molecule is a halocarbon of formula 3B

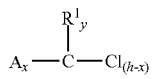

(3B)

where the carrier atom is carbon and A, R$^1$, and Cl are as described above in Formula 3. The x, y, and h are positive integers as described above. Additionally, the Cl atom could be substituted for any halogen atom in the structure.

Method of Preparing High Refractive Index Molecules

The high refractive index molecules may be prepared by any suitable method. In on embodiment, n-butyl lithium chemistry is utilized to prepare the high refractive index molecule. The conditions for carrying out such reactions is described in *J. Org. Chem.* 1998, 63, 9924-9931, which is incorporated herein by reference in its entirety. The following reaction schemes illustrate examples of suitable methods for forming high refractive index molecule.

Scheme 1 illustrates an embodiment of a method for forming a high refractive index molecule of Formula 1 comprising a sulfur-containing heterocyclic structure.

Scheme 1

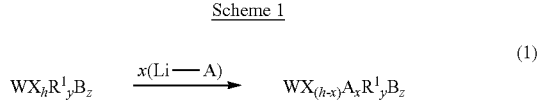
(1)

where W, B, $R^1$, x, y, z, and h are as described in Formula 1 (x=h) and X is halogen most preferably such as Cl Br, and I.

In Scheme 2, a chlorosilane is reacted with a lithiated high refractive index molecule A comprising a sulfur-containing heterocyclic structure.

Scheme 2

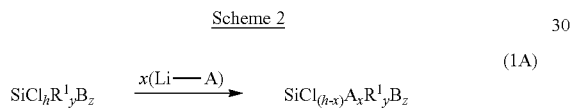
(1A)

where Si is the carrier atom, the Cl, $R^1$, and B groups are attached to the Si atom and are as described in Formula 1, and x, y, z, and h can be as described above with respect to Formula 1.

In Scheme 3, carbon is the carrier atom, and the halocarbon is reacted with a lithiated high refractive index molecule A comprising a sulfur-containing heterocyclic structure.

Scheme 3

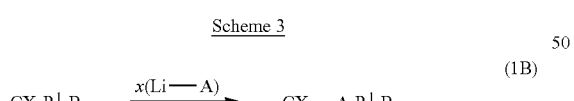
(1B)

where X, $R^1$, B, x, y, z, and h are as described in Formula 1.

The alkyl chlorosilane are useful in forming siloxane polymer repeat units M, D, and T which contain the high refractive index groups comprising the sulfur-containing heterocycles. Scheme 4 illustrates the use of a chlorosilanes to create a high refractive index group that is capable of producing a variety of M, D, and T units according to the number and selection of the $R^1$ group:

Scheme 4

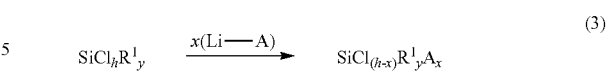
(3)

Schemes 5-7 illustrate examples of reactions in accordance with aspects of Scheme 1 that are suitable for forming high refractive index molecule. As shown in Schemes 5-7, the high refractive index group (A) is shown as a 1,2 dithiane. It will be appreciated, however, that the high refractive index group can be any suitable high refractive index group including, but not limited to, thiophene, 1,3 dithiolane, tetrahydro-2H-thiopyran, 1,4 dithane, 1,3,5 trithiane, etc.

Scheme 5 illustrates formation of a high refractive index molecule comprising a hydride functionality Scheme 5

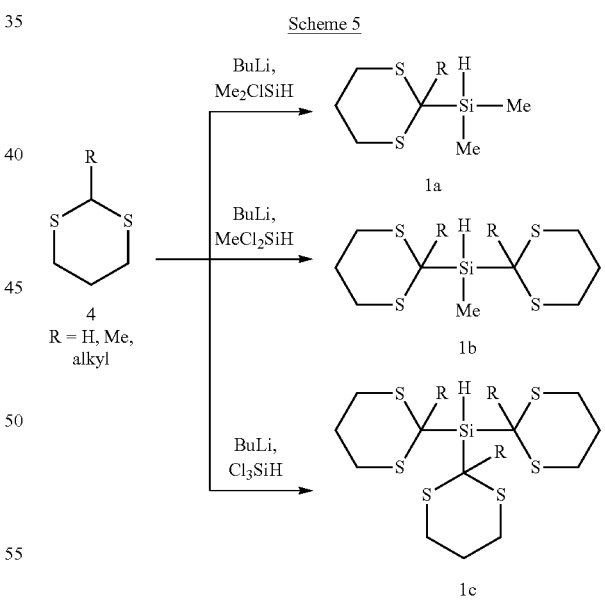

Scheme 6 illustrates examples of reactions suitable for synthesizing a high refractive index molecules comprising an allyl group Scheme 6

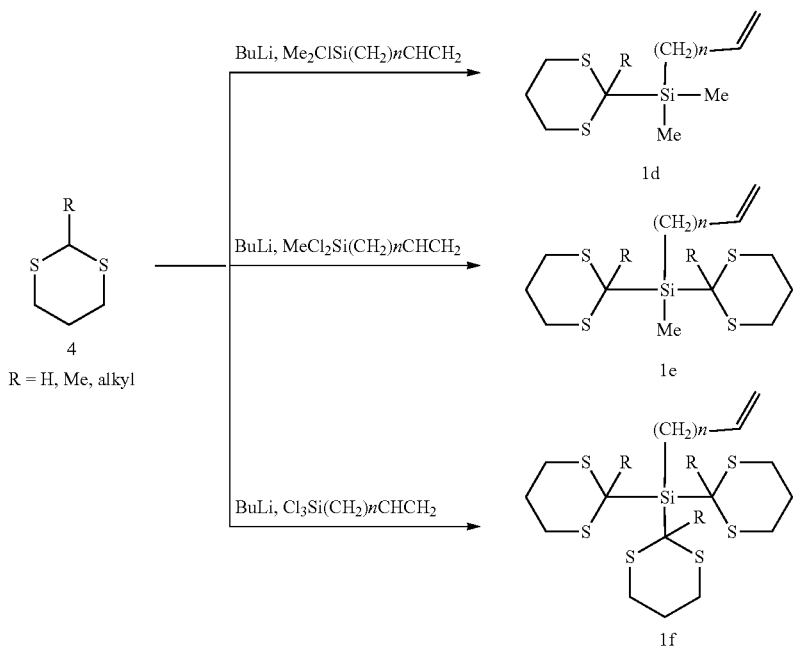

Scheme 7 illustrates examples of reactions suitable for synthesizing a high refractive index monomers comprising hydroxyl Scheme 7

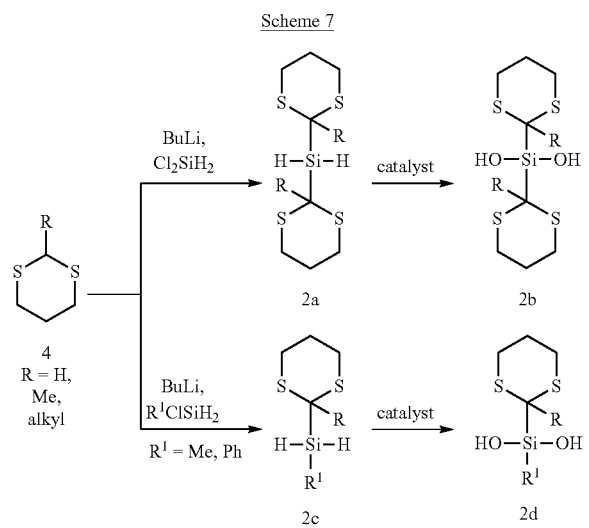

As shown in Scheme 7, the method includes first forming a hydride containing ligand using n-butyl lithium chemistry. The hydride is then converted into silanols, 2b and 2d. There are a number of catalysts known in the literature for converting 2a, 2b (and similar structures) into 2b, 2d respectively. One such catalyst is based on ruthenium (J. Am. Chem. Soc. 2000, 122, 12011-12012).

While the reactions illustrated in Schemes 5-7 illustrate specific examples employing the use of 1,3 dithiane as the sulfur-containing heterocyclic compound, methyl as an optional substituent, and silicon as the carrier atom, it will be appreciated that the reactions are not limited to these materials and any suitable carrier or sulfur-containing heterocyclic compound may be used, along with any other suitable substituent as may be desired for a particular purpose or intended use.

High Refractive Index Polymer Material

As described above, the high refractive index polymer material comprises a polymer having a high refractive index group attached thereto, where most cases the high refractive index group includes a sulfur-containing heterocycle.

Generally, the high refractive index polymer can be described containing any of the previously described M, D, T, and Q units. Thus, polymers containing the high refractive index molecules are of the general structure of Formula 4:

$$M^1_k M^2_j D^1_a D^2_b D^3_d D^4_e T^1_c T^2_i Q_f \quad (4)$$

where each monomer unit ($M^1$, $M^2$, $D^1$, $D^2$, etc.) have independently selected $R^2$-$R^7$ groups, which are chosen from hydrogen, hydroxyl, a linear or branched alkyl radical, a linear or branched alkoxy radical, an aryl radical, an alkylvinyl radical, amide, amino-groups, propyl-mercapto groups, glycidyl-containing groups, a high refractive index sulfur-containing heterocyclic compound, or a high refractive index molecule pendant group, where at least one R group on one of the monomer units is either a high refractive index molecule, as described by Formula 1, or a sulfur-containing heterocyclic compound as described by the Sulfur-Containing High Refractive Index Group; a is from 1-1000, b is from 0-500, c is from 0-500, d is from 0-100, e is from 0-100, f is from 0-100, g is from 1-1000, h is from 0-1000, and i is from 0 to 200.

In one embodiment, a high refractive index siloxane polymer may be described by linear or resinous variants of Formula 4:

$$MD_a D^{OL}_d D^H_e T_c Q_f M,$$

$$M^H D_a D^{Ph}_b D^{OL}_d D^H_e T_c Q_f M^H,$$

$MD_a D^{OL}{}_d D^{vi}{}_g T_c Q_f M$ $M^H D_a D^{Ph}{}_b D^{OL}{}_d D^{vi}{}_g T_c Q_f M^H$, $M^{vi} D_a D^{OL}{}_d D^{vi}{}_g T^{OL}{}_i Q_f M^{vi}$, $M_k M^H{}_j D_a D^{OL}{}_d T_c Q_f$ $M_k T_c T^{OL}{}_i Q_f$, $M_k D^{OL}{}_d T_c Q_f$, or $M_k M^{OL}{}_j D_a T_c Q_f$, where M, D, T, and Q are described above. In the above embodiments, "vi" represents a vinyl radical, "OL" (optical ligand) represents a sulfur-containing heterocyclic compound or a high refractive index molecule of Formula 1 comprising a sulfur-containing heterocyclic compound, $M^{vi}$ represents a dialkylvinylmonosiloxy, $D^{OL}$ represents monomer unit containing a high refractive index molecule, where one or both of the of the alkyl is either a high refractive index molecule or a sulfur containing heterocyclic compound as described earlier, $D^H$ represents an alkyl hydrogen siloxy, $D^{vi}$ represents alkylvinylsiloxy. The degree of polymerization of the high refractive index siloxane polymer is not particularly limited and can be selected as desired for a particular purpose or intended use. In one embodiment, the polymer can contain from 1 to about 10,000 repeating units. In one embodiment, a is from about 0 to about 2000, b is from about 0 to about 1000, c is from about 0 to about 1000, and d is from about 1 to about 1000, f is from about 0 to 100, g is from 1 to 50 and h is from 0 to 50.

In one embodiment, the sulfur-containing heterocyclic structure is present in the high refractive index polymer in an amount of from about 1 to about 40 mol %; from about 2.5 to about 30 mol %; from about 5 to about 25 mol %, or even from about 10 to about 20 mol %. Here as elsewhere in the specification and claims, numerical values may be combined to form new and non-disclosed ranges.

In one embodiment, a modified siloxane of the formula $MD_a D^{OL}{}_d D^H{}_e M$ comprises a high refractive index monomer ($D^{OL}$) containing a repeat unit that contains a molecule of formula 1 where, in this instance, B is a vinyl group (structure 1g). The degree of loading of 1g is chosen such that b is 5-30 and c is 0-10. $R^2$ and $R^3$ in 1g are chosen from methyl, 1,3,5 trithiane, 1,3-dithianes, and 1,3 dithiolane. Table 1 shows non-limiting embodiments of 1g with various $R^2$ and $R^3$ groups.

1g

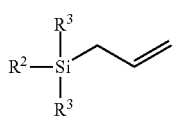

TABLE 1

| $R^2$ | $R^3$ |
| --- | --- |
| 1,3,5 trithiane | methyl |
| methyl | 1,3,5 trithiane |
| 1,3,5 trithiane | 1,3,5 trithiane |
| 1,3 dithiolane | methyl |
| methyl | 1,3 dithiolane |
| 1,3 dithiolane | 1,3 dithiolane |

TABLE 1-continued

| $R^2$ | $R^3$ |
| --- | --- |
| 1,3 dithiane | 1,3 dithiane |
| 1,3 dithiane | methyl |
| methyl | 1,3 dithiane |

In one embodiment, the high refractive index polymer material may further comprise refractive index modifying groups other than the sulfur-containing heterocyclic groups. For example, phenyl containing heterocycles may be employed in conjunction with sulfur-containing heterocyclic structures and high refractive index monomers used in accordance with the present invention. The concentration of such other refractive index modifying groups may be chosen as desired to control or modify the properties of the polymer material. The high refractive index polymer materials comprising a plurality of sulfur-containing heterocyclic structures as the high refractive index groups exhibit high refractive index values and avoid the problems associated with the use of phenyl containing high refractive index groups. Thus, in one embodiment, the present invention allows for the concentration of phenyl containing high refractive index groups to be significantly reduced. In one embodiment, the present invention allows for the elimination of phenyl containing groups from high refractive index polymers. In one embodiment, the high refractive index polymer material is substantially free of phenyl containing groups.

Method for Forming High Refractive Index Polymer

The polymer backbone is not particularly limited and may be selected based on the desired properties of the polymer material. In one embodiment, the polymer backbone is a siloxane polymer. The manner in which the polymer is formed or functionalized with the high refractive index compound may be chosen based on the desired end product and manner in which the refractive index compound is distributed on the polymer.

In one embodiment, the high refractive index polymer is produced by grafting a high refractive index monomer onto the polymer backbone. Under such a method, a siloxane polymer is provided having hydride groups, alkene groups, or another group that is reactive with an high refractive index monomer, and thus high refractive index monomer is grafted onto the polymer backbone via hydrosilylation chemistry.

In one embodiment, the siloxane can be a silicon hydride containing siloxane having the formula $MD_a D^H{}_e M$, where M, D, and $D^H$ are as described above, and a and e are positive integers. In one embodiment, a hydride containing siloxane may be represented by the formula 5:

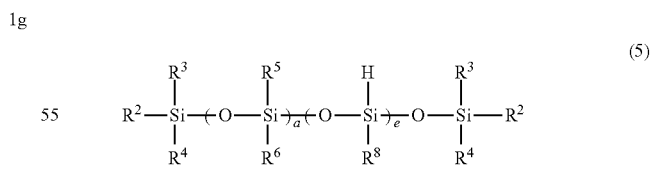

where $R^2$-$R^6$ are as descried above. The substitution $R^8$ can be described similarly as described earlier for $R^2$-$R^7$ groups. In example 5, a and e are integers having values sufficient to provide the polymer with a suitable viscosity. In one embodiment, the polymer has a viscosity of from about 0.001 to 100 PaS at 25° C. or even 0.001 to $10^6$ PaS at 25° C.

The siloxane can also be a vinyl-containing siloxane. In one embodiment, the siloxane is a vinyl-containing polysiloxane having a viscosity of from about 0.001 to $10^6$ PaS 25° C. In one embodiment, the siloxane may be exemplified by the general formula $MD_aD^{vi}{}_gM$, where M, D, and are described earlier. In one embodiment, the vinyl-containing siloxane can be a siloxane of the formula (6):

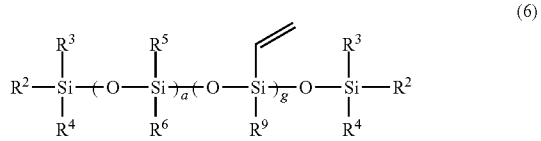

(6)

where $R^2$-$R^6$ are as descried above. The substitution $R^9$ can be described similarly as described earlier for $R^1$-$R^7$ groups. In example 6, a and g are integers having values sufficient to provide the polymer with a suitable viscosity.

The hydrosilylation reaction is typically carried out using a catalyst, e.g., a platinum or rhodium based catalyst. The art of hydrosilylation is well documented in the literature (*Angewandte Chemie, International Edition*, 2012, 51, 3225-3230 and references there-in). In one embodiment, a hydride containing or vinyl containing siloxane can be reacted with an high refractive index monomer comprising a sulfur-containing saturated heterocycle as follows

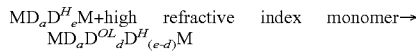

or

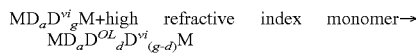

where the respective M and D components are as described above.

Scheme 8 illustrates an example of a reaction scheme for grafting a high refractive index monomer comprising an alkene group attached to the carrier atom to a polymer comprising hydride functionality.

Scheme 8

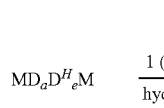

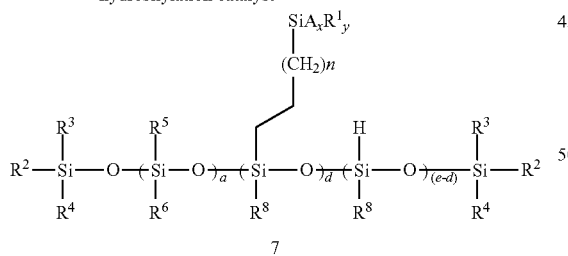

In scheme 8, $R^1$-$R^6$ and $R^8$ are groups as illustrated above and x+y=3.

Scheme 9 illustrates a reaction scheme for grafting a hydride containing high refractive index monomer to a polymer comprising alkene groups.

Scheme 9

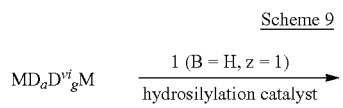

-continued

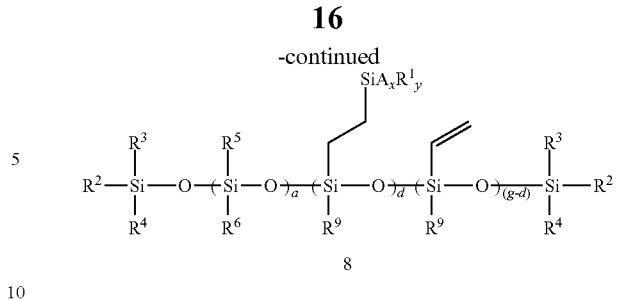

In scheme 9, $R^1$-$R^6$ and $R^9$ are groups as illustrated above and x+y=3. It will be appreciated that Schemes 8 and 9 are merely illustrative examples of methods for forming a polymer material comprising a high refractive index and does not limit the specific materials shown therein. For example, any alternative carrier atom in the pendant group could be substituted (instead of silicon as shown) and any suitable hydride or vinyl containing siloxane and any suitable sulfur-containing high refractive index compound (or high refractive index monomer) may be used as the reactants.

In another embodiment, the high refractive index monomers can be incorporated into the polymer as part of a repeating block in a block copolymer. This may be accomplished by hydrosilylation of a cyclic siloxane with an appropriate high refractive index monomer and then subjecting the modified cyclic siloxane to acid or base catalyzed ring opening polymerization to prepare high refractive index silicone polymer.

In one embodiment, a hydride containing cyclic siloxane is functionalized with the optical ligand and the resulting monomer is equilibrated to make siloxanes that contain repeating blocks of optical ligands as illustrated with the polymer 10 towards the synthesis of 11 and 12 in Scheme 10.

Scheme 10

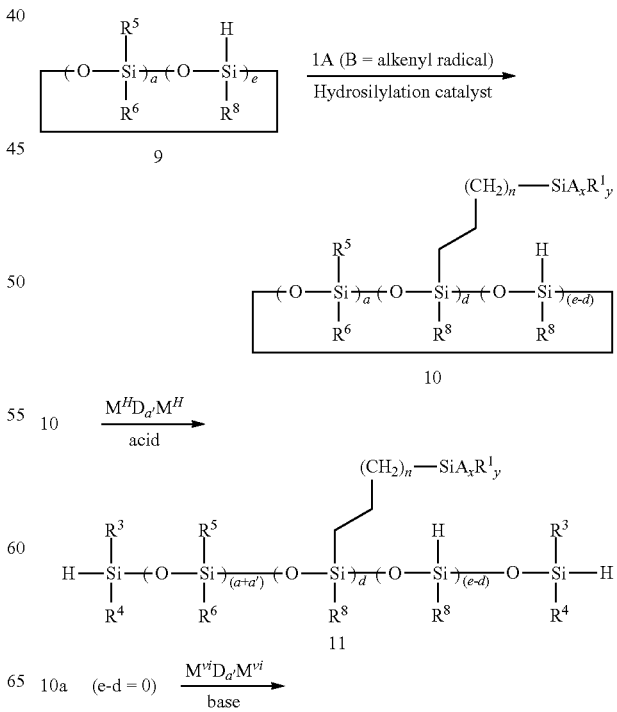

-continued

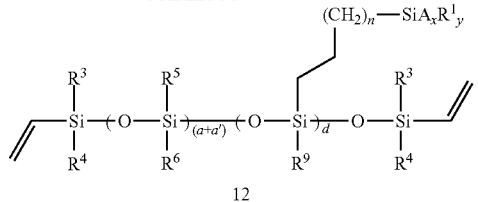

12

In one embodiment, a vinyl containing cyclic siloxane is functionalized with an optical ligand and the resulting monomer is equilibrated to make siloxanes that contain repeating blocks of optical ligands as illustrated with the polymer 13 towards the synthesis of 14 and 15 in Scheme 11.

Scheme 11

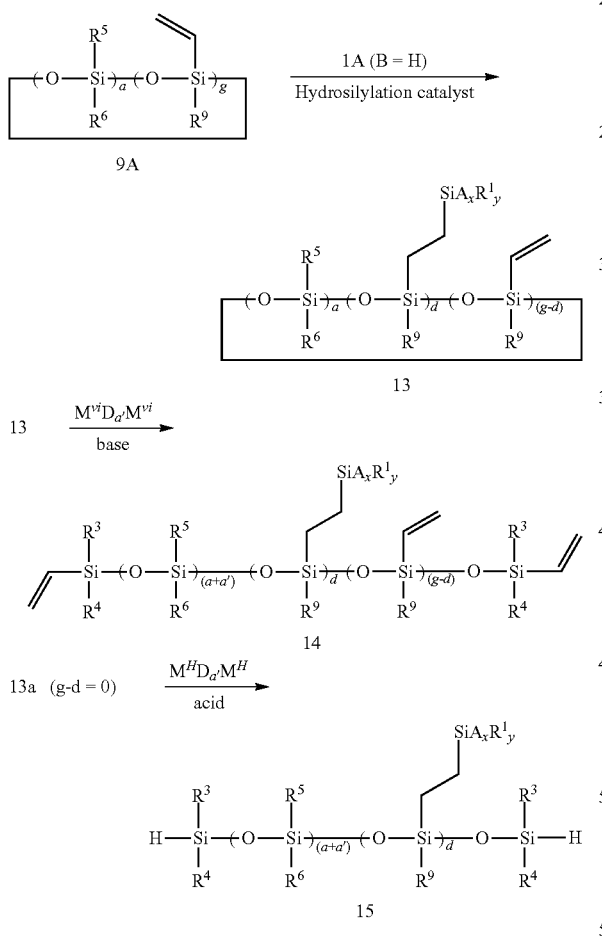

It will be appreciated that the reaction illustrated in Scheme 10 and 11 are not limited to the particular reactants and components shown therein. The high refractive index monomer may utilize other sulfur-containing saturated heterocyclic compounds or carrier atoms.

In still another embodiment, the high refractive index polymer comprises a high refractive index group attached directly to a silicon atom in the backbone of the polymer. This may be accomplished by incorporating a high refractive index monomer directly into the polymer backbone. The high refractive index monomer may be incorporated into the backbone via hydrosilylation chemistry or base catalyzed polymerization. Such methods are illustrated in Schemes 12 and 13. Scheme 12 illustrates a reaction scheme for incorporating a high refractive index monomer into the backbone via a hydrosilylation reaction.

Scheme 12

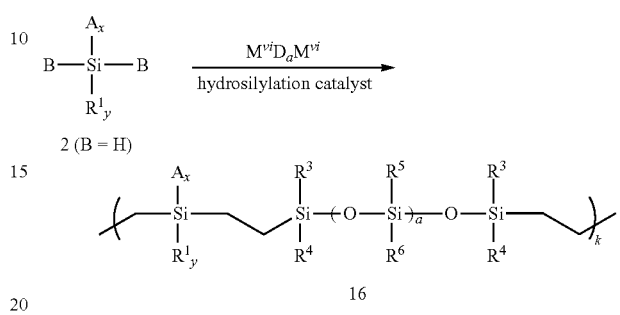

16

Scheme 13 illustrates a reaction scheme for incorporating a high refractive index monomer into the backbone via a base catalyzed reaction.

Scheme 13

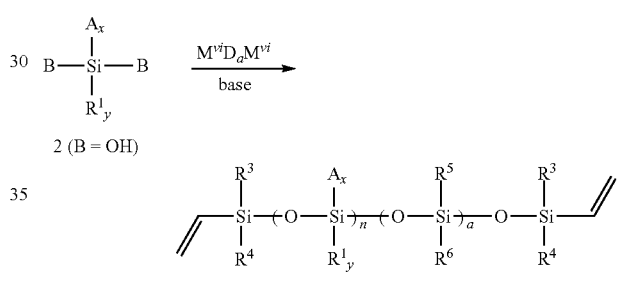

17

The high refractive index polymers of the general structure $M_kD_aT_cQ_f$ can also be prepared directly from the optical ligands containing M, D, and T units as represented by example 3 (Scheme 4). The number of chlorines present in 3 determines the final structure of the various chlorosilanes as described in Scheme 14.

Scheme 14

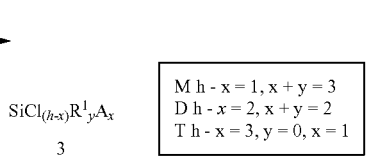

These monomers can then be reacted to form siloxane polymers through the condensation of HCl with the addition of water to form a variety of polymeric siloxane structures, including, but not limited to: linear polymers (polymerization of "D" units, capped with an "M" on either side), branched polymers ("D" and "T" units), or resinous systems ("T" units; or "M" and "Q" units; "T" and "Q" units, etc.)

Applications

The high refractive index polymers comprising a sulfur-containing high refractive index group can be used to make a variety of materials for a variety of applications. The high refractive index polymers in accordance with aspects of the invention can be used to form coatings or films that can be applied to the surface of other materials or that can be used to form products of a desired shape. The high refractive index monomers and polymers formed therefrom exhibit high refractive indexes and excellent mechanical properties and also avoid other problems associated with polymers comprising phenyl groups as the high refractive index component. The present polymers can be used in a variety of applications including, but not limited to, contact lenses, intraocular lenses solid state lighting encapsulants (light emitting diodes, organic light emitting diodes, laser diodes), waveguides (both planar and "fiber" geometries), optical computing, optical storage media, antireflection coatings, conformal coatings, optical lenses, microlenses, automobile topcoats, paint formulations and topcoats, hair care products, gradient refractive index optical components, dynamic gradient refractive index components, etc.

Aspects of the invention may be further understood with respect to the following examples. The examples are for the purpose of illustrating various aspects and embodiments of the invention and are not intended to limit the scope of the invention.

EXAMPLES

Example 1

Synthesis of High Refractive Index Molecule

A high refractive index molecule (18) is formed according to reaction Scheme 15:

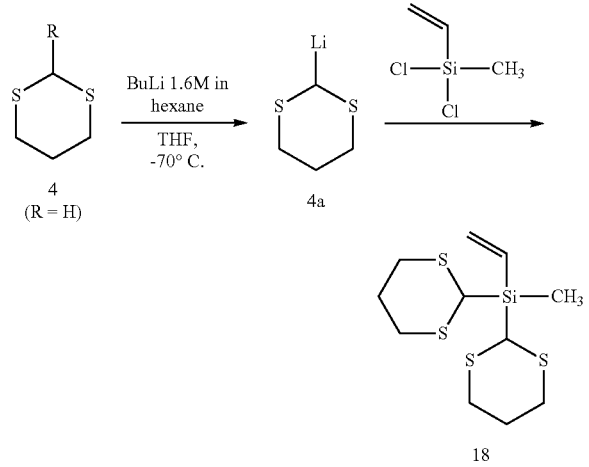

A 250 mL two-necked round-bottomed flask equipped with magnetic stirrer, J-KEM, and nitrogen inlet/out let is charged with 1,3-dithiane (4, 3.58 g, 29.8 mmol, 2.10 equiv) followed by anhydrous tetrahydrofuran (35 mL). The solution is cooled to below −70° C. (dry ice acetone bath). A solution of n-butyllithium (19.5 mL, 31.2 mmol, 2.2 equiv, 1.6 M solution in hexanes) is added via a syringe at a rate such that the bath temperature remains below −65° C. Once the addition of butyllithium was complete, the bath is held at below −65° C. for 1 hour. vinylmethyldichlorosilane (2.0 g, 14.2 mmol, 1 equiv) is added drop wise via a syringe such that the batch remains <−65° C. Once the addition of chlorosilane is complete, the batch is held for 1 hour at below −65° C. The batch is then quenched with saturated aqueous $NaHCO_3$ solution (5 mL) while maintaining the batch at below −65° C. The reaction mixture is then transferred into a separatory funnel and diluted with EtOAc (100 mL). The aqueous layer is saved. The organic layer is washed with water (2×10 mL), brine (1×10 mL). The combined aqueous waste was manifested into a waste stream. The organic layer is dried (using $MgSO_4$), filtered, and concentrated on a rotatory evaporator to obtain crude product. The material is then triturated with hexane (20 mL), and the solid is filtered over a Buckner funnel and washed with hexane (2×5 mL), dried under high vacuum to obtain 18 (3.2 g, 66% yield). The analytical data ($^1H$ NMR, $^{13}C$ NMR, $^{29}Si$, MS) confirms the compound 18.

Example 2

Synthesis of Polymer Grafted with High Refractive Index Molecule

A polymer grafted with an high refractive index molecule is prepared according to Scheme 16:

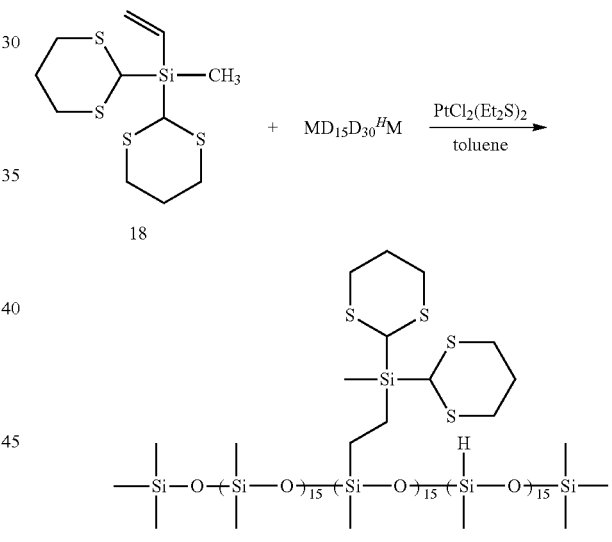

A 50 mL round bottomed flask equipped with reflux condenser and a nitrogen inlet/outlet is charged with a hydride siloxane fluid (500 mg, 0.162 mmol, 1 equiv), compound 18 (752 mg, 2.44 mmol, 15 equiv), and toluene (3.2 mL). The hydride siloxane fluid is of the formula $MD_{15}D_{30}{}^{H}M$ where M is trimethylsiloxane, D is dimethylsiloxane, and $D^H$ is methylsiloxane A stock solution of $PtCl_2(Et_2S)_2$ catalyst (0.4 mL, 0.0016 mmol, 0.01 equiv, 1.85 mg/mL of catalyst in toluene) is added to the flask and the resulting clear mixture is heated at 100° C. of oil bath temperature for 4.5 hours. The reaction mixture is then passed through a 0.45-micron syringe filter. The filtrate is concentrated on a rotatory evaporator and the residue is dried (5 hours, 55° C.@8.4 in Hg) to obtain a gum (19, 1.2171 g, 97%). Analytical data ($^1H$ NMR, $^{13}C$ NMR, $^{29}Si$) corresponds to the desired structure. The material is further purified by first dissolving into toluene (2 mL) and then precipitating the polymer by addition of hexanes (10 mL). The precipitated polymer is then dissolved into chloroform (5 mL) and the solution is concentrated on a rotatory evaporator. The oily product is then dried in a vacuum oven (65° C., 5 hours@8.2 in Hg) to obtain a gum like clear transparent polymer (763 mg, 61% yield). The polymer has a refractive index of 1.5540.

Embodiments of the invention have been described above and, modifications and alterations may occur to others upon the reading and understanding of this specification. The invention and any claims are intended to include all modifications and alterations insofar as they come within the scope of the claims or the equivalent thereof.

What is claimed is:

1. A polysiloxane polymer or copolymer having a siloxane backbone and comprising a group derived from a molecule comprising a carrier atom and a high refractive index functional group, the molecule having the formula:

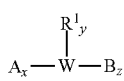

(1)

where W is the carrier atom, $R^1$ is independently chosen from hydrogen, hydroxyl, or a group containing C1-C30 carbon atoms chosen from a linear or branched alkyl radical, a linear or branched alkoxy radical, an alkylvinyl radical (including allyl), a cycloalkyl radical, a branched or linear alkenyl radical, a cycloalkenyl radical, a linear or branched alkynyl radical, an aryl radical, a substituted aryl radical, or a polynuclear aromatic group; A is chosen from a high refractive index group comprising a sulfur-containing heterocyclic structure having 2 or 3 sulfur atoms in a single ring structure; B is chosen from a halide, alkoxy (OR), hydroxyl, an alkylvinyl radical (including allyl), hydrogen, —$(CH_2)_n$SH, —$(CH_2)_n$NH$_2$, a glycidyl radical, or a combination of two or more thereof; W is silicon; n is 1-10; x is at least 1; y ranges from zero to two less than the valence of the carrier atom; z is at least 1; 1≤x+y≤one less than the valence of the carrier atom; and x+y+z is equal to the valence of the carrier atom; and wherein the sulfur-containing heterocyclic structure-containing repeating units are present in an amount of from 0.1 to 40 mol % based on the total number of repeating units in the polymer.

2. The polymer of claim 1, wherein the carrier atom of the molecule is incorporated into the backbone of the polymer and the high refractive index functional group is pendent to the carrier atom.

3. The polymer of claim 1 having a refractive index of at least 1.42.

4. The polymer of claim 1 having a refractive index of at least 1.50.

5. The polymer of claim 1 having a refractive index of at least 1.55.

6. The polymer of claim 1 having a refractive index of at least 1.60.

7. The polymer of claim 1 having a refractive index of from 1.42 to about 1.65.

8. The polymer of claim 1, wherein the polymer is described by the formula $M^1_k M^2_j D^1_a D^2_b D^3_d D^4_e T^1_c T^2_i Q_f$ (4)

where $M^1$ and $M^2$ are independently $R^2R^3R^4SiO_{1/2}$; $D^1$, $D^2$, $D^3$, and $D^4$ are independently $R^5R^6SiO_{2/2}$; $T^1$ and $T^2$ are independently $R^7SiO_{3/2}$; Q is $SiO_{4/2}$; $R^2$-$R^7$ groups are independently chosen from hydrogen, hydroxyl, a linear or branched alkyl radical, a linear or branched alkoxy radical, an aryl radical, an alkylvinyl radical, amide, amino-groups, propyl-mercapto groups, glycidyl-containing groups, a high refractive index sulfur-containing heterocyclic structure, or a high refractive index molecule pendant group, where at least one of $R^2$-$R^7$ is chosen from (1) A, optionally $R^1$ in Formula 1, or (2) the sulfur-containing heterocyclic structure; a is from 1-1000, b is from 0-500,c is from 0-500, d is from 0-100, e is from 0-100, f is from 0-100, k is from 1-1000, j is from 0-1000, and i is from 0 to 200.

9. The polymer of claim 1, wherein the polymer is described by the formula $MD_a D^{OL}_d D^H_e T_c Q_f M$, $M^H D_a D^{Ph}_b D^{OL}_d D^H_e T_c Q_f M^H$, $M^H D_a D^{Ph}_b D^{OL}_d T_c Q_f M^H$, $MD_a D^{OL}_d D^{vi}_g T_c Q_f M$, $M^{vi} D_a D^{OL}_d D^{vi}_g T_c Q_f M^{vi}$, or $M^{vi} D_a D^{OL}_d T_c Q_f M^{vi}$, where M represents a trialkylsiloxy radical or a dialkylvinylsiloxy, Q is $SiO_{4/2}$; T is $R^7SiO_{3/2}$ where $R^7$ is independently chosen from hydrogen, hydroxyl, a linear or branched alkyl radical, a linear or branched alkoxy radical, an aryl radical, an alkylvinyl radical, amide, amino-groups, propyl-mercapto groups, glycidyl-containing groups, a high refractive index sulfur-containing heterocyclic compound, or a high refractive index molecule pendant group, where at least one of $R^7$ is chosen from (1) a high refractive index heterocyclic molecule of Formula 1, or (2) a sulfur-containing heterocyclic compound; $D^{OL}$ represents an alkylsiloxy comprising a high refractive index monomer, $D^H$ represents an alkyl hydrogen siloxy, $D^{vi}$ represents alkylvinylsiloxy, D represents dialkylsiloxy, $M^{vi}$ represents a dialkylvinyl siloxy, $M^H$ represents a dialkylhydrogen radical, and a, b, c, d, e, f, and g are positive integers.

10. A composition comprising the polymer of claim 1.

11. The composition of claim 10, wherein the polymer is a copolymer comprising polydimethyl siloxane, polydiphenysiloxane, or polymethylphenylsiloxane.

12. The composition of claim 10, where the composition is a curable siloxane composition.

13. The curable composition of claim 12 further comprising an antioxidant.

14. The curable composition of claim 12 further comprising a thermal stabilizer.

15. The curable composition of claim 12 further comprising a UV stabilizer.

16. The curable composition of claim 12 further comprising an adhesion promoter.

17. The curable composition of claim 12 further comprising a platinum group metal catalyst in an amount of about 1-100 ppm.

18. The curable composition of claim 12 further comprising an inhibitor.

19. The curable composition of claim 12 further comprising a filler.

20. The composition of claim 10, wherein the composition is a coating composition.

21. The composition of claim 10, where the composition is chosen from an antireflection coating, a conformal coating, a paint formulation, and a personal care product formulation.

22. A device comprising the composition of claim 10.

23. The device of claim 22, where the device is chosen from a light emitting diode, an organic light emitting diode, a laser diode, a waveguide, an optical computing device, an optical storage medium, an optical lens, a microlens, a paint formulations, a gradient refractive index optical component, and a dynamic gradient refractive index components.

24. The polymer of claim 1 wherein the amount is from about 2.5 to about 30 mol %.

25. The polymer of claim 1 wherein the amount is from about 5 to about 25 mol %.

26. The polymer of claim 1 wherein the amount is from about 10 to about 20 mol %.

27. A composition comprising a copolymer having siloxane backbone and comprising:
(a) polydimethyl siloxane, polydiphenysiloxane, or polymethylphenylsiloxane; and
(b) a group derived from a molecule comprising a carrier atom and a high refractive index functional group, the molecule having the formula:

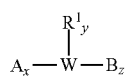
(1)

where W is the carrier atom, $R^1$ is independently chosen from hydrogen, hydroxyl, or a group containing C1-C30 carbon atoms chosen from a linear or branched alkyl radical, a linear or branched alkoxy radical, an alkylvinyl radical (including allyl), a cycloalkyl radical, a branched or linear alkenyl radical, a cycloalkenyl radical, a linear or branched alkynyl radical, an aryl radical, a substituted aryl radical, or a polynuclear aromatic group; A is chosen from a high refractive index group comprising a sulfur-containing heterocyclic structure having 2 or 3 sulfur atoms in a single ring structure; B is chosen from a halide, alkoxy (OR), hydroxyl, an alkylvinyl radical (including allyl), hydrogen, $-(CH_2)_n SH$, $-(CH_2)_n NH_2$, a glycidyl radical, or a combination of two or more thereof; W is silicon; n is 1-10; x is at least 1; y ranges from zero to two less than the valence of the carrier atom; z is at least 1; $1 \leq x+y \leq$ one less than the valence of the carrier atom; and x+y+z is equal to the valence of the carrier atom; and
wherein the sulfur-containing heterocyclic structure-containing repeating units are present in an amount of from 0.1 to 40 mol % based on the total number of repeating units in the polymer.

28. The composition of claim 27, where the composition is a curable siloxane composition.

29. The curable composition of claim 28 further comprising at least one selected from the group consisting of: an antioxidant, a thermal stabilizer, a UV stabilizer, an adhesion promoter, a platinum group metal catalyst in an amount of about 1-100 ppm, an inhibitor, and a filler.

30. The composition of claim 27, wherein the composition is a coating composition.

31. The composition of claim 27, where the composition is chosen from an antireflection coating, a conformal coating, a paint formulation, and a personal care product formulation.

32. A device comprising the composition of claim 27.

33. The device of claim 32, where the device is chosen from a light emitting diode, an organic light emitting diode, a laser diode, a waveguide, an optical computing device, an optical storage medium, an optical lens, a microlens, a paint formulations, a gradient refractive index optical component, and a dynamic gradient refractive index components.

34. A curable siloxane composition comprising a polymer having siloxane backbone and comprising:
(a) at least one selected from the group consisting of: a thermal stabilizer, a UV stabilizer, an adhesion promoter, a platinum group metal catalyst in an amount of about 1-100 ppm, an inhibitor, and a filler; and
(b) a group derived from a molecule comprising a carrier atom and a high refractive index functional group, the molecule having the formula:

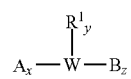
(1)

where W is the carrier atom, $R^1$ is independently chosen from hydrogen, hydroxyl, or a group containing C1-C30 carbon atoms chosen from a linear or branched alkyl radical, a linear or branched alkoxy radical, an alkylvinyl radical (including allyl), a cycloalkyl radical, a branched or linear alkenyl radical, a cycloalkenyl radical, a linear or branched alkynyl radical, an aryl radical, a substituted aryl radical, or a polynuclear aromatic group; A is chosen from a high refractive index group comprising a sulfur-containing, aliphatic, heterocyclic structure having 2 or 3 sulfur atoms in a single ring structure; B is chosen from a halide, alkoxy (OR), hydroxyl, a alkylvinyl radical (including allyl), hydrogen, $-(CH_2)_n SH$, $-(CH_2)_n NH_2$, a glycidyl radical, or a combination of two or more thereof; W is silicon; n is 1-10; x is at least 1; y ranges from zero to two less than the valence of the carrier atom; z is at least 1; $1 \leq x+y \leq$ one less than the valence of the carrier atom; and x+y+z is equal to the valence of the carrier atom; and
wherein the sulfur-containing, aliphatic, heterocyclic structure-containing repeating units are present in an amount of from 0.1 to 40 mol % based on the total number of repeating units in the polymer.

35. The curable composition of claim 34 further comprising an antioxidant.

* * * * *